United States Patent
Racz et al.

(10) Patent No.: US 9,333,323 B2
(45) Date of Patent: May 10, 2016

(54) STYLET ASSEMBLIES, CATHETER KITS AND ASSEMBLIES INCLUDING STYLET ASSSEMBLIES, AND RELATED METHODS

(75) Inventors: Sandor N. Racz, Coppell, TX (US); Gabor J. Racz, Dallas, TX (US)

(73) Assignee: Custom Medical Applications, Inc., Johnstown, NY (US)

( * ) Notice: Subject to any disclaimer, the term of this patent is extended or adjusted under 35 U.S.C. 154(b) by 0 days.

(21) Appl. No.: 14/354,527

(22) PCT Filed: Oct. 28, 2011

(86) PCT No.: PCT/US2011/001828
§ 371 (c)(1),
(2), (4) Date: Apr. 25, 2014

(87) PCT Pub. No.: WO2013/062504
PCT Pub. Date: May 2, 2013

(65) Prior Publication Data
US 2014/0296828 A1   Oct. 2, 2014

(51) Int. Cl.
*A61M 25/00* (2006.01)
*A61M 25/01* (2006.01)

(52) U.S. Cl.
CPC ....... *A61M 25/0102* (2013.01); *A61M 25/0097* (2013.01)

(58) Field of Classification Search
CPC .................... A61M 25/0102; A61M 25/0097; A61M 25/0014; A61M 2025/0063; A61M 25/0043
See application file for complete search history.

(56) References Cited

U.S. PATENT DOCUMENTS

| | | |
|---|---|---|
| 3,727,613 A | 4/1973 | Sorenson et al. |
| 3,860,006 A | 1/1975 | Patel |
| 4,191,186 A | 3/1980 | Keeler |
| 4,304,231 A | 12/1981 | Bodicky et al. |
| 4,362,156 A | 12/1982 | Feller et al. |
| 5,163,912 A | 11/1992 | Gay et al. |
| 5,226,427 A | 7/1993 | Buckberg et al. |
| 5,242,389 A | 9/1993 | Schrader et al. |
| 5,250,035 A | 10/1993 | Smith et al. |
| 5,300,045 A | 4/1994 | Plassche |
| 5,496,281 A | 3/1996 | Krebs |
| 5,542,916 A | 8/1996 | Hirsch et al. |

(Continued)

FOREIGN PATENT DOCUMENTS

| | | |
|---|---|---|
| EP | 856332 A1 | 8/1998 |
| EP | 620022 A1 | 2/1999 |

(Continued)

OTHER PUBLICATIONS

PCT International Preliminary Report on Patentability, PCT/US2011/001828 dated May 8, 2014.

(Continued)

*Primary Examiner* — Bradley Osinski
(74) *Attorney, Agent, or Firm* — TraskBritt, P.C.

(57) ABSTRACT

Stylet assemblies include one or more securing members extending from a base portion of the stylet assembly and configured to removably attach to a portion of an associated structure. Catheter kits and catheter assemblies may include such stylet assemblies. Methods of using a catheter assembly may include inserting at least a portion of a stylet coupled to a stylet cap in a catheter associated with a catheter connection and securing a portion of the stylet cap to only a portion of the catheter connection hub.

18 Claims, 5 Drawing Sheets

(56) References Cited

U.S. PATENT DOCUMENTS

| | | |
|---|---|---|
| 5,957,912 A | 9/1999 | Heitzmann |
| 6,027,461 A * | 2/2000 | Walker et al. .................. 600/585 |
| 6,206,870 B1 | 3/2001 | Kanner |
| 6,245,029 B1 | 6/2001 | Fujita et al. |
| 6,652,491 B1 * | 11/2003 | Walker et al. ............ 604/164.01 |
| 6,755,794 B2 | 6/2004 | Soukup |
| 7,931,591 B2 | 4/2011 | Mccarthy et al. |
| 7,931,594 B2 | 4/2011 | Hirsh |
| 2005/0090801 A1 * | 4/2005 | Racz et al. ..................... 604/500 |
| 2008/0183154 A1 | 7/2008 | Racz et al. |
| 2009/0105638 A1 | 4/2009 | Partlett |
| 2009/0112167 A1 | 4/2009 | Haarala et al. |
| 2009/0187140 A1 | 7/2009 | Racz |
| 2009/0292259 A1 | 11/2009 | Delano et al. |
| 2009/0292273 A1 | 11/2009 | Racz et al. |

FOREIGN PATENT DOCUMENTS

| | | |
|---|---|---|
| EP | 1033146 A2 | 7/2002 |
| EP | 2002858 A2 | 12/2008 |
| JP | 2827203 A | 11/1998 |
| JP | 2005512669 A | 5/2005 |
| JP | 2007222387 A | 9/2007 |
| JP | 2008518672 A | 6/2008 |
| JP | 2008246203 A | 10/2008 |
| JP | 2008307386 A | 12/2008 |
| JP | 2011504403 A | 2/2011 |
| JP | 5819537 | 10/2015 |
| WO | 9518575 A1 | 7/1995 |
| WO | 9731677 A1 | 9/1997 |
| WO | 9952585 A1 | 10/1999 |
| WO | 03030985 A2 | 4/2003 |
| WO | 2004018015 A2 | 3/2004 |
| WO | 2006062636 A1 | 6/2006 |
| WO | 2006099306 A2 | 9/2006 |
| WO | 2010022370 A1 | 2/2010 |
| WO | 2013062504 A1 | 5/2013 |

OTHER PUBLICATIONS

International Search Report for International Application No. PCT/US2011/001828, mailed May 29, 2012, 4 pages.

International Written Opinion for International Application No. PCT/US2011/001828, dated May 24, 2012, 6 pages.

Partial European Search Report for copending application EP 11 87 4693, dated Dec. 15, 2014.

Canadian Examination Search Report for copending application CA 2,853,756 dated Dec. 3, 2015.

* cited by examiner

STYLET ASSEMBLIES, CATHETER KITS AND ASSEMBLIES INCLUDING STYLET ASSSEMBLIES, AND RELATED METHODS

CROSS-REFERENCE TO RELATED APPLICATION

This application is a national phase entry under 35 U.S.C. §371 of International Patent Application PCT/US2011/001828, filed Oct. 28, 2011, designating the United States of America and published in English as International Patent Publication WO 2013/062504 A1 on May 2, 2013.

TECHNICAL FIELD

Embodiments of the disclosure relate generally to stylet assemblies and stylets for use with catheter assemblies. More specifically, embodiments of the disclosure relate to stylet assemblies including stylet caps that enable a distal end of the stylet to be consistently located at or near a distal end of the catheter during insertion, placement, and repositioning.

BACKGROUND

During insertion and placement of a conventional catheter, a stylet is typically positioned within the catheter to provide stiffness and structural strength. The stylet may enable an otherwise flexible catheter to be more precisely controlled (e.g., steered) during insertion and placement of the catheter. After initial placement of the catheter, the stylet may be withdrawn and a catheter connector hub through which fluids may be introduced to the catheter may be attached to an external end of the catheter. Catheter connector hubs typically include a connection portion such as, for example, a Luer taper connection for providing a secure connection with a fluid-introducing device, such as a hypodermic syringe. After connection of the catheter connector hub, the stylet may be reinserted through the connection portion of the catheter connector hub into the catheter. The stylet may provide stiffness and structural strength during any repositioning of the catheter. Conventionally, an external end of the stylet may be embedded within a stylet cap (also known in the art as a stylet hub), which may retain the external end of the stylet outside the catheter. Accordingly, the stylet cap may enable the stylet to reinforce the catheter, to be easily withdrawn from the catheter, and to be inserted into the catheter without risk of mistakenly and irretrievably inserting the end of the stylet into the catheter. However, the stylet cap may also prevent a distal end of the stylet from reaching a distal end of the catheter, leaving the leading distal end of the catheter flexible and difficult, if not impossible, to control.

DISCLOSURE

Described are stylet assemblies including a stylet secured to a base portion. The stylet is sized and adapted for insertion at least partially into a catheter associated with a corresponding catheter connection hub. The base portion includes at least two securing members extending therefrom that are configured to removably attach to the catheter connection hub.

In some embodiments, the present disclosure includes a stylet assembly including a base portion and a stylet extending from and secured to the base portion. The stylet is sized and adapted for insertion at least partially into a catheter associated with a corresponding catheter connection hub. The stylet assembly further includes at least two securing members extending from the base portion and configured to removably attach to a portion of the catheter connection hub.

In additional embodiments, the present disclosure includes a catheter kit including a catheter having a proximal end and a distal end, a catheter hub for connection to the catheter's proximal end, and the stylet assembly of claim 1 for at least partial insertion into the catheter and catheter hub proximate the catheter's proximal end.

In yet additional embodiments, the present disclosure includes a catheter assembly. The catheter assembly includes a catheter comprising a proximal end and a distal end, and a catheter hub connected to the catheter's proximal end where the catheter hub comprises an annular connection portion at an end thereof. The catheter assembly further includes a stylet assembly comprising a stylet configured for insertion through the catheter hub and into the catheter at the distal end of the catheter; and a stylet cap having the stylet secured thereto. The stylet cap comprises a base portion and at least one securing member extending from the base portion and configured to removably attach to only a portion of the annular connection portion of the catheter connection hub.

In yet additional embodiments, the present disclosure includes a method of using a catheter assembly. The method includes inserting at least a portion of a stylet coupled to a stylet cap in a catheter associated with a catheter connection hub having an annular connection portion at one end thereof and securing a portion of the stylet cap to the catheter connection hub comprising engaging at least one securing member of the stylet cap with only a portion of the annular connection portion of the catheter connection hub.

In yet additional embodiments, the present disclosure includes a stylet assembly including a stylet sized and adapted for use with a catheter associated with a corresponding catheter connection hub and an integral structure formed from a polymer. The integral structure includes a base portion and a central elongate member extending from the base portion and having the stylet secured thereto. The central elongate member is configured to be received by a receiving portion of the corresponding catheter connection hub in such a manner to contain the stylet within the catheter. The integral structure further includes at least two discrete securing members extending from the base portion in a generally parallel manner to the central elongate member. The at least two securing members are configured to removably attach to the corresponding catheter connection hub.

In yet additional embodiments, the present disclosure includes a stylet assembly including a stylet sized and adapted for use within a catheter and an integral structure attached to the stylet, the integral structure formed from a polymer. The integral structure includes a base portion having the stylet extending therefrom and secured thereto and at least two discrete securing members extending from the base portion in a generally parallel manner. Each of the discrete securing members comprises a protrusion on a distal end thereof and the protrusion of each discrete securing member extends from the discrete securing member in a direction toward the stylet.

DETAILED DESCRIPTION

The drawings are not necessarily to scale and relative dimensions may have been exaggerated for the sake of clarity. Additionally, elements common between figures may retain the same or similar numerical designation.

The disclosure generally relates to catheter assemblies, stylets, and stylet assemblies used with catheter assemblies. More specifically, embodiments of the disclosure relate to stylet assemblies including a stylet cap that enable a distal end of a stylet to be consistently located at or near a distal end of the catheter during insertion, placement, and repositioning.

Figure 1:
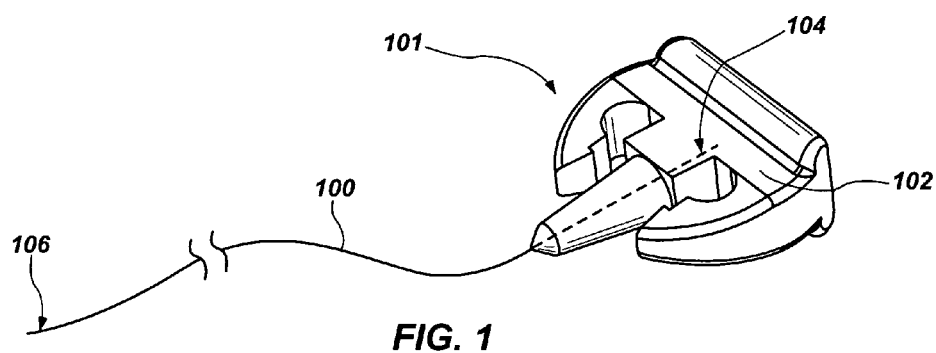
FIG. 1 is a perspective view of a stylet assembly including a stylet and a stylet cap connected to an end of the stylet in accordance with an embodiment of the present disclosure.
Figure 4:
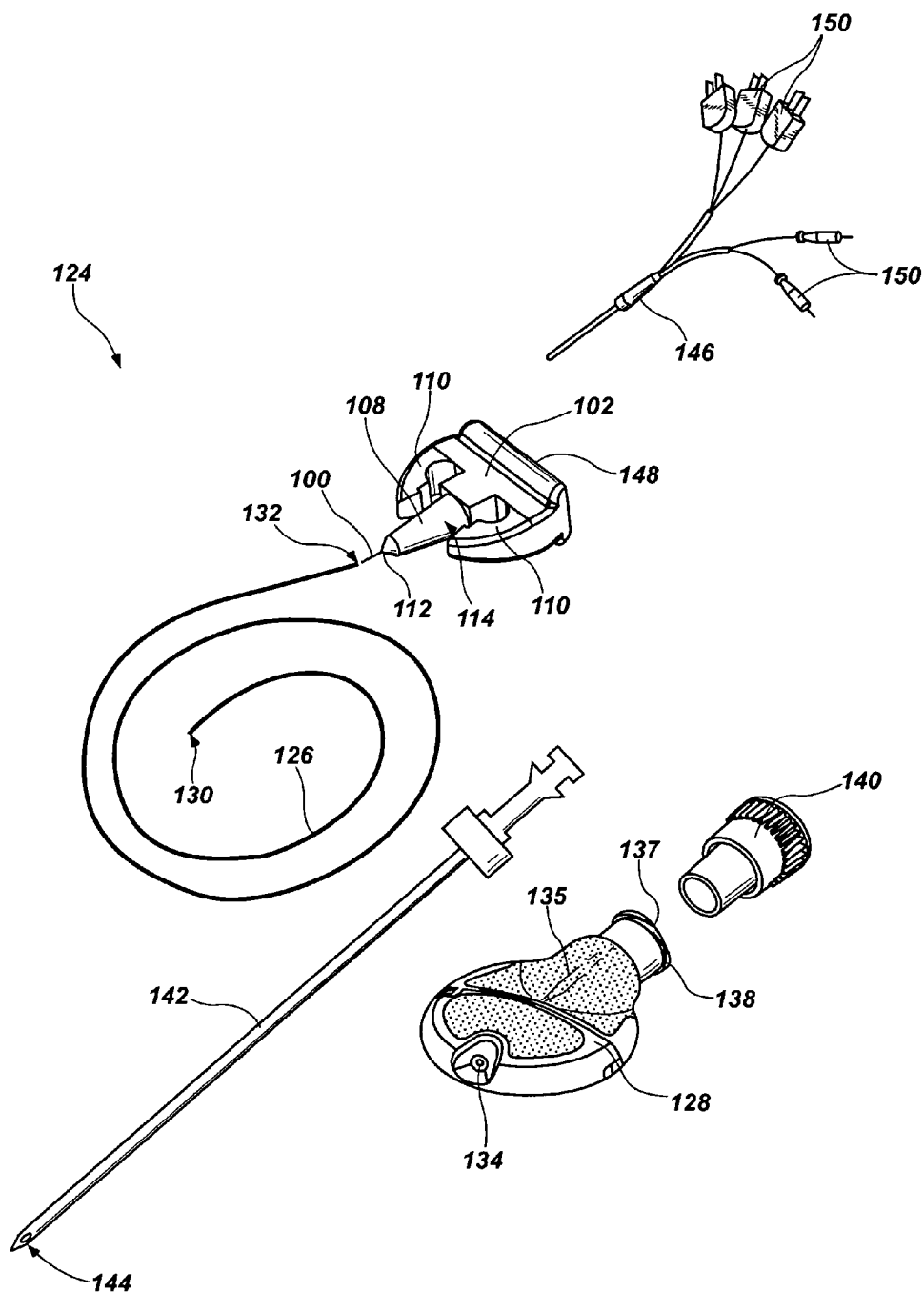
FIG. 4 illustrates a perspective view of a catheter kit including a catheter, a (prior art) catheter connection hub, a stylet, and a stylet cap in accordance with another embodiment of the present disclosure.

Referring to FIG. 1, a perspective view of a stylet assembly including a stylet 100 and a stylet cap 102 connected to a proximal end 104 of the stylet 100 is shown. Stylets may be as described in, e.g., U.S. Patent Application Publication 2005/0090801 A1, published Apr. 28, 2005, the disclosure of which is hereby incorporated herein in its entirety by this reference. The stylet 100 may be sized and adapted for use with a catheter associated with a corresponding catheter connection hub 128 (FIG. 4). The proximal end 104 of the stylet 100 is shown in dashed lines because it is located within, and secured to or otherwise fixedly associated with, the stylet cap 102. The stylet 100 extends from and is secured to a portion of the stylet cap 102 (e.g., a base portion 118) to a distal end 106. The stylet 100 typically comprises an elongated member configured to increase the stiffness and/or structural strength of another structure or device, such as, for example, a catheter (e.g., catheter 126 of FIG. 4), in which the stylet 100 may be inserted. In such an embodiment, the stylet 100 may comprise a wire, a tube, a plurality of intertwined or interwoven wires, or a plurality of intertwined or interwoven tubes (see, e.g., U.S. Patent Application Publication 2009/0187140 A1, published Jul. 23, 2009), the disclosure of which is hereby incorporated herein in its entirety by this reference. In some embodiments, the stylet may also include at least one of materials and means for enhanced RF, resistance heating, thermocouple, and microwave apparatus, as well. The stylet 100 may comprise a material suitable for use in medical fields, such as, for example, medical grade stainless steel or medical grade titanium.

Figure 2:
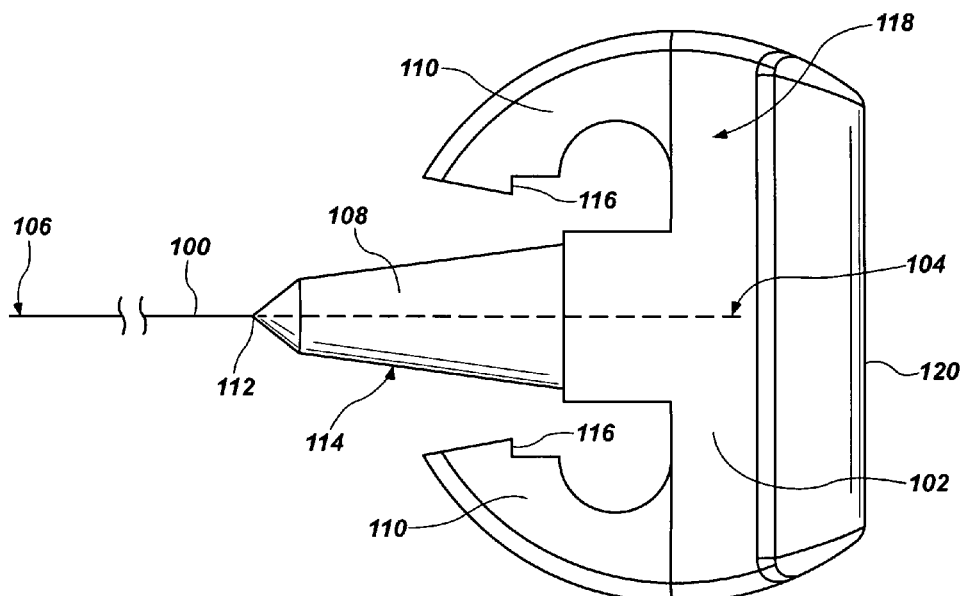
FIG. 2 is a plan view of the stylet cap and a portion of the stylet 100 shown in FIG. 1.

Referring to FIG. 2, a plan view of the stylet cap 102 and a portion of the stylet 100 of FIG. 1 is shown. The base portion 118 of the stylet cap 102 may include a central member 108 (e.g., an elongate member) extending from the base portion 118, and one or more (in some embodiments, preferably at least two) securing members 110 associated with or connected to and flanking the central member 108 for engaging (e.g., removably attaching) another structure of a catheter assembly (e.g., a portion of the catheter hub 128 (FIG. 4)). The depicted stylet 100 extends from a tip 112 of the central member 108 and is secured to a portion of the stylet cap 102 (e.g., the base portion 118). In such an embodiment, the depicted stylet 100 extends from its proximal end 104 located within the stylet cap 102, through the central member 108, and beyond the tip 112 of the central member 108 to a distal position. In some embodiments, the central member 108 may be adapted to be at least partially received within a portion of a catheter connection hub such as, for example, the catheter connection hub 128 shown and described below with reference to FIG. 4. In such embodiments, the central member 108 may include a male taper portion 114 (e.g., a male Luer taper portion). The male taper portion 114 preferably conforms to features and specifications defined in International Organization for Standardization (ISO) 594 standards, and specifically ISO standard 594-1:1986. The depicted male taper portion 114 is configured for insertion into a reciprocal or corresponding portion of another structure or device, such as, for example, a taper portion of the catheter hub 128 (FIG. 4). In other embodiments, such as that described below with reference to FIGS. 9 and 10, the stylet cap may not include a central member protruding from the base portion. In yet other embodiments, the stylet cap may include a truncated central member as compared to that shown in FIG. 2.

As shown in FIG. 2 and in some embodiments, the stylet cap 102 may include more than one securing member 110. For example, the stylet cap 102 may include two, three, four, or even more securing members 110. In other embodiments, the stylet cap 102 may include only a single securing member 110. In embodiments where the stylet cap 102 includes a plurality of securing members 110, the securing members 110 may be located at least substantially at angularly equidistant locations about the stylet cap 102 from one another. For example, the securing members 110 may be located 180° from one another where the stylet cap 102 includes two securing members 110, as in the embodiment shown in FIG. 2 (e.g., the stylet cap 102 may be substantially symmetric). As another example, the securing members 110 may be located 120° from one another where the stylet cap includes three securing members 110. In some embodiments, the securing members 110 may extend substantially parallel to each other (and, in some embodiments, substantially parallel to the central member 108) and offset from the central member 108. In other words, the securing members 110 will typically flank the central member 108.

The securing members 110 may be configured to removably attach to another structure or device, such as, for example, the catheter hub 128 shown in FIG. 4. For example, each securing member 110 may include a protrusion 116 (e.g., a hook) extending from a portion of the securing member 110 (e.g., proximate a distal end of the securing member 110). The protrusion 116 may extend from the securing member 110 in a direction toward the central member 108. The protrusion 116 may cooperatively engage with a portion of the catheter hub 128 (FIG. 4) (e.g., a recess or another protrusion formed therein). In some embodiments, the securing members 110 may be formed to enable the securing members 110 to deform (e.g., substantially elastic deformation). For example, the securing members 110 may be formed of a material with sufficient flexibility (e.g., toughness) that the securing members 110 bend outward from the central member 108 as the securing members 110 are brought into engagement with the other structure or device (e.g., catheter hub 128 of FIG. 4), and may return to substantially the initial position of the securing members 110 as the protrusions 116 reach the corresponding recess formed in the other structure or device. That is, while the securing members 110 may experience a small amount of plastic deformation, the securing members 110 have a toughness that enables them to return to a position where they can be attached to an associated structure after having been deformed during attachment or removal one or more times. In addition, the securing members 110 may be sufficiently flexible that the protrusions 116 may disengage from the corresponding recess formed in the other structure or device in response to sufficient force applied by a user. In other words, the securing members 110 may form a cantilever portion of the stylet cap 102 that may be partially deformed to engage with a corresponding structure (connection portion 138 of the catheter hub 128 (FIG. 4)). In some embodiments, the securing members 110 may comprise a portion having a relatively smaller width or cross-sectional area as compared to an adjacent portion of the securing member 110 (e.g., a distal end of the securing member 110). The portion of the securing member 110 having a relatively smaller width or cross-sectional area may comprise a point of flexure of the securing member 110 as it is deformed during attachment or removal from the catheter hub 128 (FIG. 4). In some embodiments, the securing members 110 may be formed such that the protrusion 116 of the securing members 110 may be at least partially threaded on a portion of another structure (e.g., connection portion 138 of the catheter hub 128 (FIG. 4) formed as a threaded portion as discussed below). In some embodiments, the securing members 110 may be formed to enable both deformation and threading of the securing members 110 in order to removably attach the stylet cap 102 to another structure or device.

Figure 3:
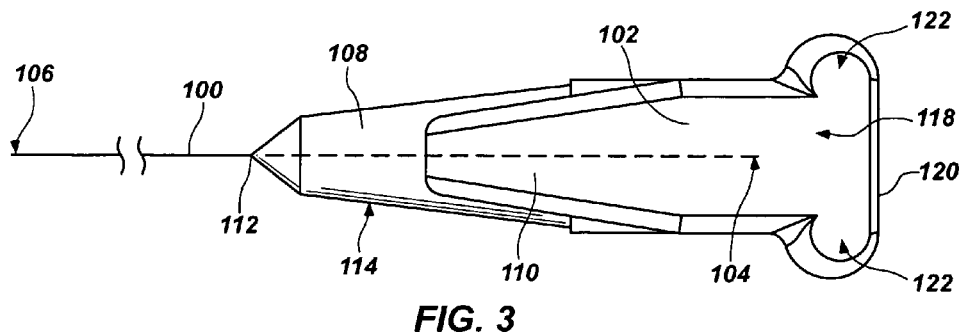
FIG. 3 depicts a side view of the stylet cap and a portion of the stylet 100 shown in FIG. 1.

The central member 108 and the securing members 110 may extend from a base portion 118 of the stylet cap 102 (FIGS. 2 and 3). The base portion 118 may include a rearmost surface 120 of the stylet cap 102 (FIG. 3). The central member 108 may extend farther from the rearmost surface 120 of the stylet cap 102 than the securing members 110. The proximal end 104 of the stylet 100 may be secured within the base portion 118 of the stylet cap 102. In some embodiments, the central member 108, the securing members 110, and the base portion 118 of the stylet cap 102 may comprise a single integrally formed structure in some embodiments. In other embodiments, at least one of the central members, the securing members, and the base portion comprises a separate structure that is connected to the others to form the stylet cap (not shown).

Referring specifically to FIG. 3, a side view of the stylet cap 102 of FIGS. 1 and 2 is shown. The base portion 118 of the stylet cap 102 may include gripping portions 122 formed therein. The gripping portions 122 are preferably configured to enable a user to more easily grasp and manipulate the stylet cap 102, for example, during insertion, placement, repositioning, connection to another device or structure, or disconnection from the other device or structure. The gripping portions 122 typically comprise protrusions extending from the base portion 118 in a direction transverse to the direction in which the stylet 100 extends in some embodiments, as shown in FIG. 3. In other embodiments, the gripping portions may comprise recesses formed in the base portion (not shown).

The stylet cap 102 is preferably formed of any material suitable for use in medical applications and exhibiting sufficient flex to enable connection and disconnection of the securing members 110 using a snap fit. For example, the stylet cap 102 may comprise a metal, such as, for example, medical grade stainless steel, or a polymer, such as, for example, acrylonitrile butadiene styrene (ABS). The stylet cap 102 may be formed using conventional processes known to those of ordinary skill in the art. For example, the stylet cap 102 may be formed using an injection molding process.

In some embodiments, the stylet 100 may be secured to the stylet cap 102 during formation of the stylet cap 102. For example, the stylet cap 102 may be molded around the proximal end 104 of the stylet 100. The stylet 100 may, e.g., be fixed in the mold at a set location, enabling the distal end 106 of the stylet 100 to extend a predetermined distance from the tip 112 of the stylet cap 102. In other words, the proximal end 104 of the stylet 100 may be embedded within the stylet cap 102 at, e.g., a known or set location. In other embodiments, the stylet cap 102 is formed and the stylet 100 subsequently secured to the stylet cap 102. For example, the stylet cap 102 may be formed with a bore through the central member 108 into the base portion 118. The stylet 100 may be threaded through the bore. The stylet 100 may include a bend or loop configured to retain the stylet 100 at a predetermined location within the base portion 118 of the stylet cap 102. In such an embodiment, the distal end 106 of the stylet 100 may extend a preferably predetermined distance from the tip 112 of the stylet cap 102. The proximal end 104 of the stylet 100 may then be secured within the stylet cap 102, for example, using an adhesive or using mechanical affixation. As a specific, non-limiting example, the proximal end 104 of the stylet may be secured within the stylet cap 102 using an epoxy.

Referring to FIG. 4, a perspective view of a catheter kit 124 is shown. The catheter kit 124 includes a catheter 126, a catheter hub 128 (see, e.g., U.S. Patent Application Publication 2008/0183154 A1, published Jul. 31, 2008), the disclosure of which is hereby incorporated herein in its entirety by this reference, a stylet 100, and a stylet cap 102. The stylet 100 and stylet cap 102 may be at least substantially similar to those described previously. The catheter 126 may be configured to receive the stylet 100 at least partially therein. In some embodiments, the stylet 100 may be pre-inserted into the catheter 126. For example, the distal end 106 (FIG. 3) of the stylet 100 may be located at or near a distal end 130 of the catheter 126 where the tip 112 of the stylet cap 102 abuts a proximal end 132 of the catheter 126. In other embodiments, the stylet 100 may not be pre-inserted into the catheter 126 when provided in the catheter kit 124.

As further shown in FIG. 4, the catheter hub 128 typically comprises a catheter-receiving portion 134 and a fluid coupling element 135 having a receiving portion 137 and a connection portion 138 (e.g., an annular receiving and connection portion) at an end of the fluid coupling element for coupling to another element such as, for example, a fluid source. The catheter-receiving portion 134 is depicted as configured to secure the proximal end 132 of the catheter 126 therein. Accordingly, the proximal end 132 of the catheter 126 is configured for insertion into the catheter-receiving portion 134 of the catheter hub 134.

The catheter kit 124 may optionally include any of several other structures or devices. For example, the catheter kit 124 may optionally include a needle 142, sometimes referred to in the art as a "cannula." The depicted needle 142 is configured to puncture skin using a sharpened tip 144 and comprises a hollow member through which the catheter 126 and stylet 100 may extend. As another example, the catheter kit 124 may optionally include a lead cable 146. The lead cable 146 may be configured for electrical connection to the proximal end 104 (see FIGS. 1 through 3) of the stylet 100 through an electrical connection portion 148 of the stylet cap 102. Connectors 150 on the lead cable 146 may be configured to provide a conduit for at least one of electrical power, RF signals, sensor signals, and microwave signals to the stylet 100.

Figure 5:
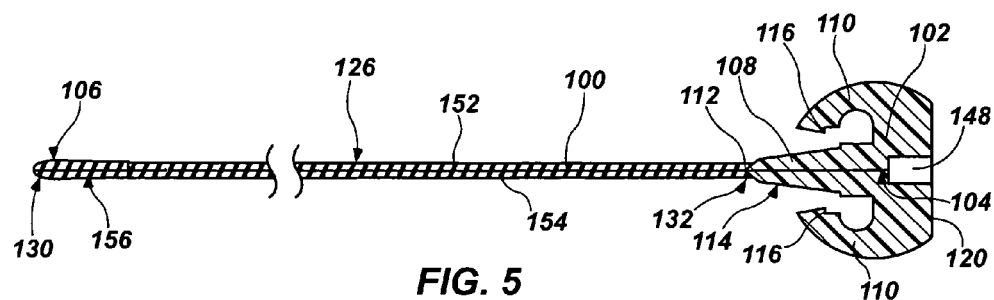
FIG. 5 is a cross-sectional view of a stylet within a catheter in accordance with yet another embodiment of the present disclosure.

Referring to FIG. 5, a cross-sectional view of a stylet 100 within a catheter 126 is shown. The catheter 126 may comprise a tube 152 configured for insertion into a patient to provide a conduit through which other devices or substances (e.g., a stylet, a probe, a fluid) may be conveyed. A coiled member 154 may be disposed within the tube 152 to resist kinking and collapsing of the tube 152, thereby enhancing the ability of the tube 152 to act as an open conduit. At the distal end of the catheter 126, the coiled member 154 may protrude from the tube 152 and, in some embodiments, the coiled member 154 may include a less-tightly coiled portion 156. The less-tightly coiled portion 156 may enable a fluid (e.g., a fluid analgesic) to more easily flow to an exterior of the catheter 126. In such an embodiment, the distal end 130 of the catheter may enable controlled and precise delivery of a substance to a desired location where the distal end 130 may be placed. The stylet 100 may extend from a proximal end 104 located within a stylet cap 102, through a central member 108 of the stylet cap 102, and beyond a tip 112 of the stylet cap 102 into the lumen of the catheter 126. In some embodiments, the stylet 100 may be inserted into the catheter 126 to reinforce the catheter 126, and a proximal end 132 of the catheter 126 may abut the tip 112 of the stylet cap 102. The stylet 100 may extend through the catheter 126 and a distal end 106 of the stylet 100 may be located substantially at the distal end 130 of the catheter 126 (e.g., flush with or protruding slightly past the distal end 130 of the catheter 126). In such an embodiment, the stylet 100 may reinforce the catheter 126 along all or substantially all of its length.

In some embodiments, the stylet cap 102 may position the stylet such that the distal end 106 of the stylet 100 extends past the terminal end of the tube 152. For example, the distal end 106 of the stylet 100 may extend into the portion of the coiled member 154 protruding from the tube 152. In some embodiments, the stylet cap 102 may position the distal end 106 of the stylet 100 proximate (e.g., near or abutting) the terminal end of the coiled member 154 protruding from the tube 152.

In use, the catheter 126 and stylet 100 are inserted into a patient. For example, a needle 142 (FIG. 4) punctures the skin of a patient and provides an initial direction for insertion and insertion depth. The distal ends 130 and 106 of the catheter 126 and the stylet 100, respectively, are inserted through the needle 142 (FIG. 4) and into the patient. The distal ends 130 and 106 of the catheter 126 and the stylet 100 may be inserted into the patient beyond the sharpened tip 144 of the needle 142 (FIG. 4) to a desired placement position. For example, the distal ends 130 and 106 of the catheter 126 and the stylet 100 are inserted into an intrathecal space of a patient to administer an analgesic. A portion of the catheter 126 proximate the distal end 130 thereof may be bent prior to insertion to enable a doctor or other medical care personnel to steer or otherwise influence the direction in which the catheter 126 proceeds in some embodiments. In other embodiments, the catheter 126 may not be handled in such a way that the catheter 126 and stylet 100 undergo plastic deformation prior to insertion through the needle 142 (FIG. 4). As a specific, non-limiting example, the catheter 126 and stylet 100 may be introduced into an epidural space of a patient through the coccyx (tailbone) for thoracic or lumbar procedures, a technique known in the art as the "Racz Method." Once the distal end 130 of the catheter 126 is placed, the stylet 100 may be withdrawn from the catheter 126 and the needle 142 may be removed from the patient over an external portion of the catheter 126.

Figure 6:
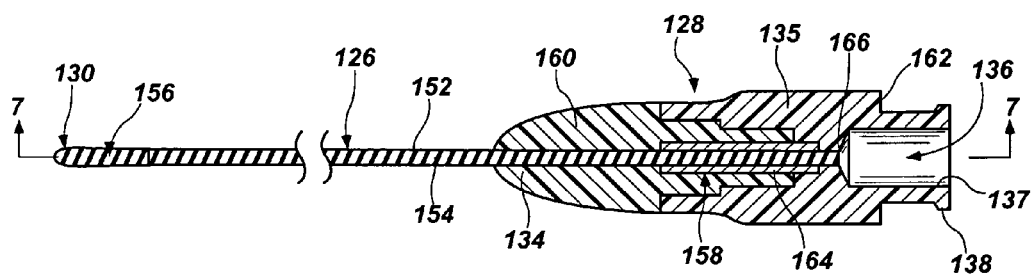
FIG. 6 depicts a cross-sectional view of the catheter of FIG. 5 after withdrawal of the stylet and connection to a catheter connection hub.

Referring to FIG. 6, a cross-sectional view of the catheter 126 of FIG. 5 after withdrawal of the stylet 100 (FIG. 5) and connection to an associated catheter connection hub 128 is shown. After the stylet 100 (FIG. 5) has been withdrawn, the proximal end 132 of the catheter 126 is shown. The catheter 126 may be inserted into a catheter hub 128 that is configured to retain the proximal end 132 of the catheter 126 therein. Exemplary catheter hubs 128 that may be connected to catheters 126 are disclosed in U.S. Patent Application Publication No. 2008/0183154, published Jul. 31, 2008 to Racz et al., the disclosure of which is hereby incorporated herein in its entirety by this reference. The proximal end 132 of the catheter 126 may be inserted into a catheter-receiving portion 134 of the catheter hub 132. The proximal end 132 of the catheter 126 may be secured within the catheter-receiving portion 134 of the catheter hub 132 using a catheter-retaining portion 158. For example, rotation of a first catheter hub member 160 relative to a second catheter hub member 162 may cause a deformable member 164 to selectively constrict or expand. Such selective constriction and expansion of the deformable member 164 may selectively secure and release the proximal end 132 of the catheter 126.

Figure 7:
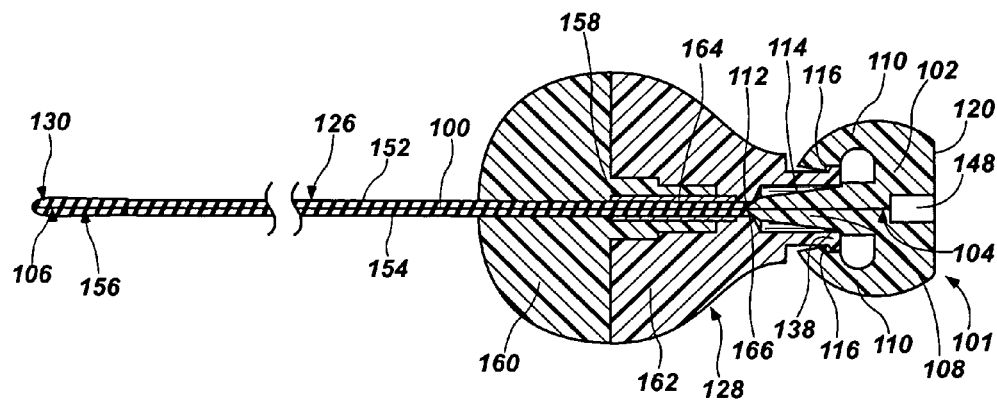
FIG. 7 illustrates a cross-sectional view of the catheter and catheter hub assembly of FIG. 6 (taken along section line 7-7 of FIG. 6) after a stylet has been inserted into the catheter through the catheter hub and a stylet cap has been removably connected to the catheter hub.

Referring now to both FIGS. 6 and 7, which shows a stylet assembly 101 partially disposed within the catheter 126 and associated catheter-receiving hub 128, the fluid coupling element 135 of the catheter hub 128 opposing the catheter-receiving portion 134 may comprise an opening 136 (e.g., formed by the receiving portion 137) for receiving a portion of the stylet assembly (e.g., the taper portion 114 of the central member 108). For example, the opening 136 may be formed by a portion of the catheter hub 128 (e.g., a female Luer taper portion) that is configured to receive the male taper portion 114 of the stylet cap 102 at least partially therein. At the end of the catheter hub 128 opposing the catheter-receiving portion 134, the catheter hub 128 may comprise the connection portion 138 (e.g., an annular connection portion 138). The connection portion 138 may comprise a protrusion (e.g., an annular protrusion) on an external portion of the catheter hub 128 proximate the opening 136. For example, the connection portion 138 may include a threaded portion (e.g., a LUER-LOK® threaded joint) for threaded engagement with a catheter hub cap 140 (FIG. 4). In some embodiments, the securing members 110 of the stylet cap 102 may only engage with a portion of the annular connection portion 138 while a remaining portion remains exposed. For example, the securing members 110 of the stylet cap 102 only engage with (e.g., abut) a portion of the annular protrusion of the connection portion 138.

The receiving portion 137 may be configured to receive the central member 108 of the stylet cap 102 at least partially therein and the stylet 100 may be contained within the catheter 126. The depicted catheter hub 128 includes an opening 136 at an end of the catheter hub 128 opposing the catheter-receiving portion 134 formed by the receiving portion 137. The opening 136 may extend within the catheter hub 128 from an external surface thereof to a location at or near a terminal end of the catheter-receiving portion 134. For example, the opening 136 may extend to a location within the catheter hub 128 that is about 0.025 inches (0.635 mm) from the catheter-receiving portion 134 at most. As another example, the opening 136 may extend to the catheter-receiving portion 134 such that there is no discernable distance between a terminal end of the opening 136 and the catheter-receiving portion 134. As a specific, non-limiting example, the opening 136 may extend to a location about 0.020 inches (0.508 mm) from the catheter-receiving portion 134. In such an embodiment, the proximal end 132 of the catheter 126 may be located at most about 0.025 inches (0.635 mm) from an end of the opening 136. In embodiments where the opening 136 extends to a location proximate the catheter-receiving portion 134, a channel 166 may connect the opening 136 to the catheter-receiving portion 134. In such an embodiment, the channel 166 may extend for about 0.025 inches or less (<0.635 mm) between the opening 136 and the catheter-receiving portion 134.

In use, the catheter connection hub 128 is connected to the proximal end 132 of the catheter 126 after the distal end 130 of the catheter 126 has been placed at what the doctor or other medical care personnel thinks is an appropriate location within the patient. Once the catheter hub 128 has been connected to the proximal end 132 of the catheter 126, another device or substance (e.g., an RF probe or a fluid analgesic) may be introduced to the patient through the catheter. For example, a hypodermic needle containing a fluid analgesic may be inserted into the catheter through the opening 136 of the catheter hub 128, and the fluid analgesic may be introduced to the patient through the catheter 126. Afterward, the catheter hub 128 may remain connected to the catheter 126 for additional administrations of the other device or substance or during repositioning of the distal end 130 of the catheter 126. For example, the catheter hub 128 may remain fixed to the proximal end 132 of the catheter 126 and may be affixed to the skin of the patient, such as with medical tape, for additional doses of fluid analgesic as previously described. The stylet 100 that had previously been withdrawn or another stylet 100 may be inserted into the catheter 126 through the catheter hub 128 to provide strength and stiffness to the catheter 126 and to obstruct access to the opening 136 of the catheter hub 128. As another example, the stylet 100 that had previously been withdrawn or another stylet 100 may be inserted into the catheter 126 through the catheter hub 128, and the distal end 130 of the catheter 126 may be repositioned within the patient. Such repositioning may be desirable where, for example, the fluid analgesic does not have its intended effect or the distal end 130 of the catheter 126 is discovered to be in an undesirable location using imaging or other monitoring technology.

Referring to FIG. 7, stylet 100 has been inserted into the catheter 126 through the catheter hub 128 and stylet cap 102 has been removably connected to the catheter hub 128. The stylet 100 inserted into the catheter 126 may be the same stylet 100 used during insertion and initial placement of the catheter 126, or may be another stylet 100. The distal end 106 of the stylet 100 may be inserted into the opening 136 of the catheter hub 128, through the channel 166 that may connect the opening 136 to the catheter-receiving portion 134 of the catheter hub 128, and into the catheter 126 extending toward the distal end 130 of the catheter 126. As the distal end 106 of the stylet 100 approaches the distal end 130 of the catheter 126, the male taper portion 114 of the stylet cap 102 may be inserted into the opening 136 of the catheter hub 128.

The securing members 110 may be removably attached to the connection portion 138 of the catheter hub 128 adjacent the opening 136 as discussed above. For example, the securing members 110 may include a protrusion 116 that removably engages with a portion of the catheter hub 128 (e.g., a LUER-LOCK® threaded joint connection portion). In such an embodiment, the securing members 110 may comprise cantilevered connection members, as discussed above, configured for removable, attachment to a connection portion 138 of a catheter hub 128. The attachment of the stylet cap 102 to the catheter hub 128 where the securing members 110 of the stylet cap 102 are substantially elastically deformable (e.g., a snap-fit) may enable a user to removably secure the stylet cap 102 to the catheter hub 128 without twisting the stylet cap 102 or otherwise unduly manipulating the stylet 100, catheter hub 128, or catheter 126, which may reduce unintentional displacement of the distal end 130 of the catheter 126 and irritation of the tissues through which the catheter extends. In addition, removable attachment of the stylet cap 102 to the catheter hub 128 may enhance the ability of the stylet 100 to resist unintentional displacement (e.g., unintentional withdrawal or partial withdrawal of the stylet) while enabling the stylet cap 102 to be attached to the catheter hub 128 quickly and easily.

When the stylet cap 102 is attached to the connection portion 138 of the catheter hub 128, the distal end 106 of the stylet 100 may be located at or near the distal end 130 of the catheter 126. For example, the distal end 106 of the stylet 100 may abut the distal end 130 of the catheter 126 in some embodiments. In other embodiments, the distal end 106 of the stylet 100 may be located 0.050 inches (1.27 mm), 0.025 inches (0.635 mm), 0.020 inches (0.508 mm), or less from the distal end 130 of the catheter 126.

The stylet cap 120 may enable the stylet 100 to reinforce all or substantially all of the catheter 126 during insertion and initial placement (FIG. 5) and during any subsequent repositioning or rest. The central member 108 and the securing members 110 may enable the distal end 106 of the stylet 100 to be consistently and securely located at or near the distal end 130 of the catheter 126 irrespective of whether the proximal end 132 of the catheter is secured within a catheter hub 128. Stated in another way, when the stylet cap 102 is attached to the connection portion 138, the stylet cap 102 may position the distal end 106 of the stylet 100 in a substantially similar location (e.g., at the same location or proximate thereto) as when the stylet 100 is inserted into the catheter 126 without the use of the catheter hub 128 (e.g., as shown in FIG. 5). For example, the central member 108 of the stylet cap 102 may be positioned proximate to (e.g., abutting) the proximal end 132 of the catheter 126 when the stylet is inserted into the catheter 126 with or without the use of the catheter hub 128. Such an embodiment may enable the distal end 106 of the stylet 100 to be placed in approximately the same position with or without the use of the catheter hub 128.

Figure 8:
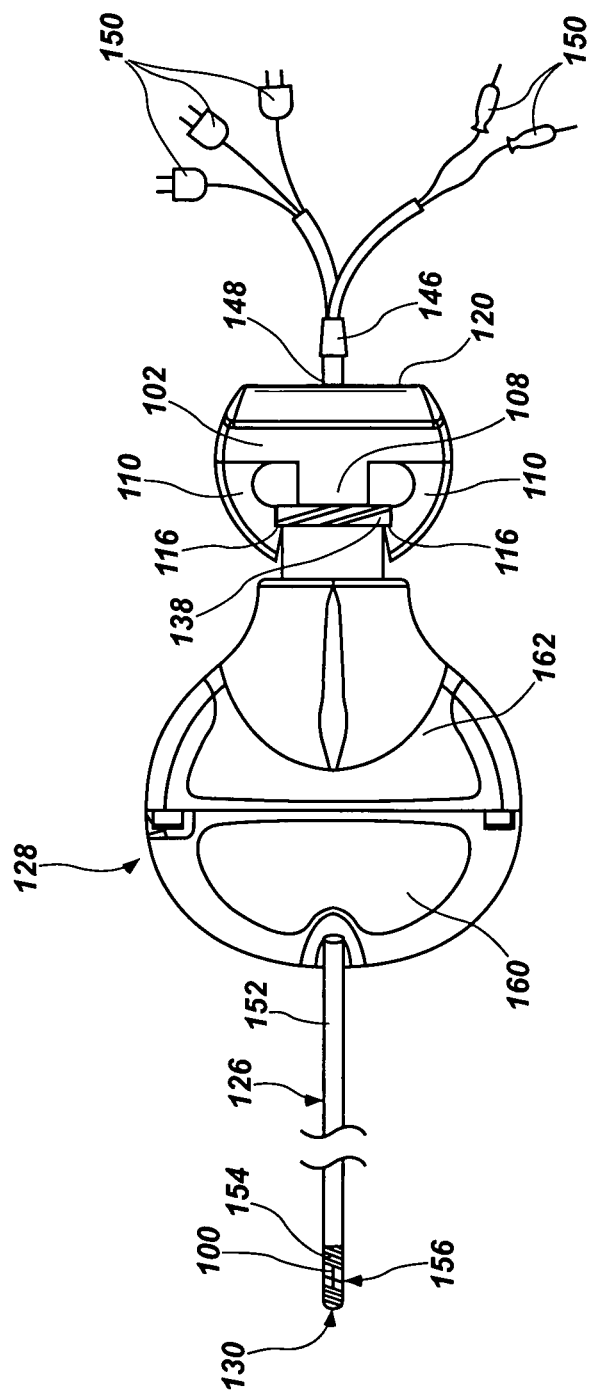
FIG. 8 illustrates a plan view of a lead cable electrically connected to a catheter assembly similar to that of FIG. 7.

Referring to FIG. 8, a plan view of a lead cable 146 electrically connected to a catheter assembly similar to that of FIG. 7 is shown. The catheter assembly comprises a catheter 126 having its proximal end 132 secured within a catheter hub 128. A stylet 100 is inserted through the catheter hub 128 toward a distal end 130 of the catheter 126. A stylet cap 102 is removably attached to the catheter hub 128 using securing members 110. The stylet 100 extends from and is secured within a central member 108 of the stylet cap 102. A proximal end 104 of the stylet 100 within the stylet cap 102 is electrically and mechanically connected to a lead cable 146 comprising a plurality of connectors 150. The lead cable 146 may be removable from or permanently attached to the stylet cap 102.

Figure 9:
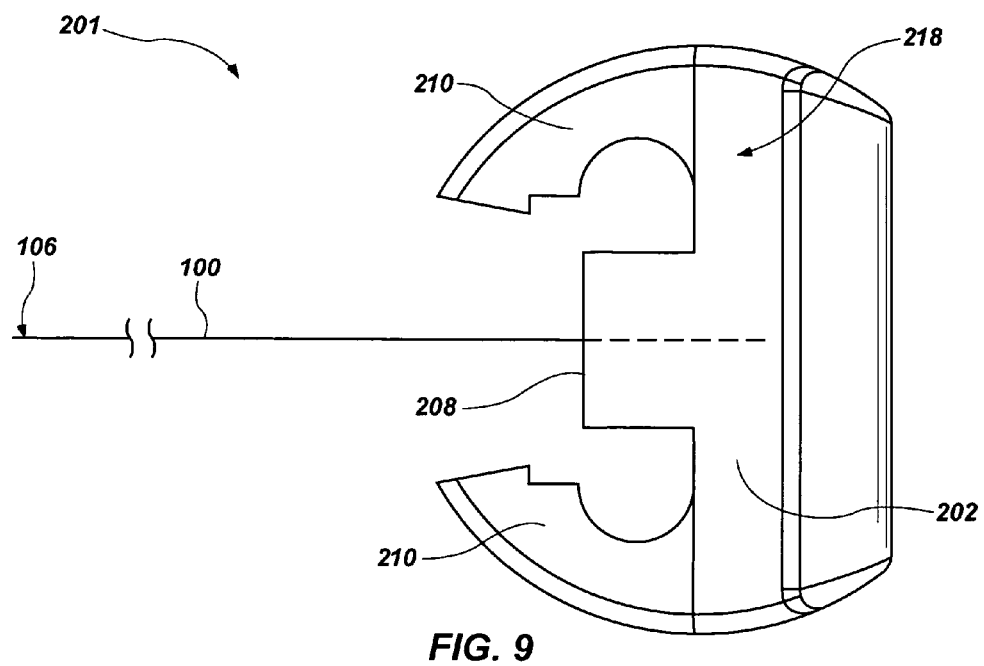
FIG. 9 is a plan view of a portion of a stylet assembly in accordance with yet another embodiment of the disclosure.
Figure 10:
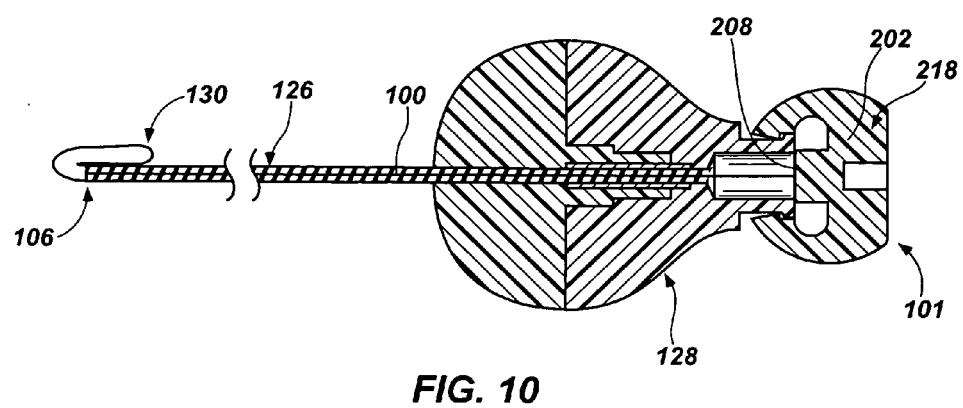
FIG. 10 illustrates a partial cross-sectional view of a catheter and a catheter hub assembly after the stylet assembly of FIG. 9 has been inserted into the catheter through the catheter hub and a stylet cap has been removably connected to the catheter hub.

FIG. 9 shows a plan view of a portion of a stylet assembly that may be somewhat similar to the stylet assembly 101 discussed above. As shown in FIG. 9, stylet assembly 201 may not include a central member or may include a truncated central member. For example, stylet assembly 201 may include a stylet 100 and stylet cap 202 and the stylet 100 may extend from the base portion 218 of the stylet cap 202 (e.g., a surface 208 of the base portion 218), but not through a central member as above. In some embodiments, the surface 208 of the base portion 218 proximate the stylet 100 may protrude from, be flush with, be recessed in, or combinations thereof relative to an adjacent surface of the base portion 218. The surface 208 of the base portion 218 may be positioned proximate to (e.g., abutting with) an associated structure (e.g., the proximal end 132 of the catheter 126 or a portion of the catheter hub 128 as shown in FIG. 10) when the stylet is received within the associated structure. In some embodiments, the surface 208 of the base portion 218 may be positioned relatively further away the distal end 106 of the stylet 100 as compared to one or more securing members 210 of the stylet cap 202. For example, the surface 208 of the base portion 218 may be recessed between the one or more securing members 210.

FIG. 10 illustrates a partial cross-sectional view of catheter 126 and catheter hub 128 assembly after the stylet assembly 201 has been inserted into the catheter 126 through the catheter hub 128 and stylet cap 202 has been removably connected to the catheter hub 128. As shown in FIG. 10, stylet assembly 201 may be inserted into the catheter 126 and removably secured to the catheter hub 128 in a manner substantially similar to that discussed above with reference to FIG. 7. As shown in FIG. 10, a portion of the stylet cap 202 may not extend proximate to the proximal end 132 of the catheter 126. For example, a portion of the stylet cap 202 may extend only partially into the catheter hub 128 or, as shown in FIG. 10, the stylet cap 202 may not extend into the catheter hub 128 and base portion 218 of the stylet cap 202 (e.g., surface 208) may abut with an outer surface of the catheter hub 128. By reducing the size of the stylet cap 202, the stylet 100 may be positioned at different locations in the catheter 126 depending on whether or not a catheter hub 128 is used. For example, when the stylet assembly 201 is inserted directly into the catheter 126 (e.g., similar to that shown in FIG. 5 and, for example, where the base portion 218 of the stylet cap 202 abuts the proximal end 132 of the catheter 126), the base portion 218 of the stylet cap 202 may enable the distal end 106 of the stylet 100 to be positioned at a first location (e.g., at or near the distal end 130 of the catheter 126). However, when the stylet assembly 201 is inserted into the catheter 126 and the catheter hub 124, as shown in FIG. 10 (e.g., where the base portion 218 of the stylet cap 202 abuts an outer surface of the catheter hub 124), the stylet cap 202 may enable the distal end 106 of the stylet 100 to be positioned at a second, different location (e.g., at a select distance from the distal end 130 of the catheter 126). In other words, the stylet cap 202 may enable the distal end 106 of the stylet 100 to be positioned at or near the distal end 130 of the catheter 126 when inserted directly into the catheter 126 and to not be positioned at or near the distal end 130 of the catheter 126 when inserted into the catheter 126 via the catheter hub 124. In such an embodiment, the relatively reduced length that the stylet 100 extends into the catheter 126 via the catheter hub 124 as compared to FIG. 7 may enable the distal end 130 of the catheter 126 to be folded over as shown in FIG. 10 (e.g., to form a relatively larger blunt end of the catheter 126).

What is claimed is:

1. A catheter kit comprising:
a catheter having a proximal end and a distal end;
a catheter connection hub for connection to the catheter's proximal end; and
a stylet assembly comprising:
a base portion;
a stylet comprising at least one wire extending from and secured to the base portion, the stylet sized and adapted for insertion at least partially into the catheter;
at least two securing members extending from the base portion and configured to removably attach to an outer, fluid coupling portion of the catheter connection hub, wherein the at least two securing members are adapted to removably attach the stylet to the catheter connection hub at only an exterior portion of the fluid coupling portion of the catheter connection hub; and
a central member extending from the base portion past a distalmost end of all of the at least two securing members such that the central member extends from the base portion a distance greater than each of the at least two securing members, the central member configured to be received by a receiving portion of the corresponding catheter connection hub in such a manner to contain the stylet within the catheter, wherein a distal end of the central member of the stylet assembly that extends past the distalmost end of all of the at least two securing members is sized and adapted to abut with a proximal end of the catheter at a first location when the stylet is received only in the catheter and the at least two securing members that extend from the base portion a lesser extent than the central member are sized and adapted to engage with the catheter connection hub having the proximal end of the catheter received therein at a second location different than the first location when the stylet is received in both the catheter and the catheter connection hub in order to position a distal end of the stylet within the catheter at a similar location when the stylet is received only in the catheter and when the stylet is received in both the connection hub and the catheter.

2. The catheter kit of claim 1, wherein the base portion and the at least two securing members are formed as an integral structure.

3. The catheter kit of claim 1, wherein the at least two securing members are formed on opposing portions of the base portion and extend from the base portion in a parallel manner.

4. The catheter kit of claim 1, further comprising a lead cable in electrical connection with the stylet.

5. The catheter kit of claim 1, wherein each discrete securing member of the at least two securing members comprises a protrusion on a distal end of the respective discrete securing member extending radially inward from the respective discrete securing member and configured to engage with of a corresponding portion of the catheter connection hub.

6. The catheter kit of claim 1, wherein the stylet is secured within the base portion and wherein the stylet exits the base portion at a location recessed between the at least two securing members.

7. The catheter kit of claim 1, wherein the stylet assembly is configured to position the stylet in the catheter such that both a portion of the catheter and a portion of the stylet within the catheter are at least partially secured by the catheter hub.

8. A catheter assembly comprising:
a catheter comprising a proximal end and a distal end;
a catheter hub connected to, the catheter's proximal end, the catheter hub comprising an annular connection portion at an end thereof; and
a stylet assembly comprising:

a stylet configured for insertion through the catheter hub and into the catheter at the proximal end of the catheter; and a stylet cap having the stylet secured thereto and comprising:
 a base portion; and
 plurality of securing members extending from the base portion, wherein the stylet cap is adapted to removably attach to the catheter connection hub at only an exterior circumference of the annular connection portion of the catheter connection hub with the plurality of securing members;
 a central member extending from the base portion, wherein a distal end of the central member extends past a distalmost end of all of the plurality of securing members;
 wherein, when the stylet of the stylet assembly is received in the catheter and the catheter hub, the stylet cap is sized and configured to position a distal end of the stylet at a first location in the catheter; and
 wherein, when the stylet of the stylet assembly is received in only the catheter, the stylet cap is sized and configured to position the distal end of the stylet at the first location.

9. The catheter assembly of claim 8, wherein the connection portion of the catheter connection hub comprises a threaded portion and wherein a distal portion of each of the plurality of securing members is configured to engage with the threaded portion.

10. The catheter assembly of claim 8, wherein the stylet cap further comprises a central member extending from the base portion a distance greater than the plurality of securing members and that is configured to be received in a receiving portion of the catheter hub.

11. The catheter assembly of claim 8, wherein the first location in the catheter is at or near the distal end of the catheter.

12. A catheter assembly comprising:
 a catheter comprising a proximal end and a distal end;
 a catheter hub connected to the catheter's proximal end, the catheter hub comprising an annular connection portion at an end thereof; and
 a stylet assembly comprising:
  a stylet configured for insertion through the catheter hub and into the catheter at the proximal end of the catheter; and
  a stylet cap having the stylet secured thereto and comprising:
   a base portion;
   at least one securing member extending from the base portion and configured to removably attach to only an exterior circumference of the annular connection portion of the catheter connection hub; and
   a central member that is configured to be received in a receiving portion of the catheter hub;
  wherein, when the stylet of the stylet assembly is received in the catheter and the catheter hub, the stylet cap is sized and configured to position a distal end of the stylet at a first location in the catheter;
  wherein, when the stylet of the stylet assembly is received in only the catheter, the stylet cap is sized and configured to position the distal end of the stylet at the first location; and
  wherein, when the stylet assembly is partially received within the catheter hub, the stylet cap is sized and configured to position a distal end of the central member at a distance between 0.020 inches (0.508 mm) and 0.025 inches (0.635 mm) from the proximal end of the catheter.

13. A catheter assembly comprising:
 a catheter having a proximal end and a distal end;
 a catheter connection hub for connection to the catheter's proximal end; and
 a stylet assembly comprising:
  a stylet; and
  an integral structure formed from a polymer and comprising:
   a base portion;
   a central elongate member extending from the base portion in a first direction away from the base portion and having the stylet secured thereto, the central elongate member configured to be received by the catheter connection hub in such a manner to contain the stylet within the catheter; and
   at least two discrete securing members extending from the base portion in the first direction in a parallel manner to the central elongate member, wherein each discrete securing member comprises a protrusion on a distal end thereof extending radially inward from the discrete securing member and configured to engage with of a corresponding portion of the catheter connection hub, wherein the central elongate member extends past the protrusion on the distal end of all of the at least two discrete securing members, the at least two securing members configured to removably attach only to an outer circumference of a fluid connection portion of the catheter connection hub to attach the stylet to the catheter connection hub, wherein the stylet assembly is sized and adapted to abut with the catheter at the central elongate member of the integral structure and engage with the catheter connection hub with the at least two discrete securing members in order to position a distal end of the stylet within the catheter at a similar location when the stylet is received only in the catheter and when the stylet is received in both the connection hub and the catheter.

14. The catheter assembly of claim 13, wherein the base portion is configured to receive a user's fingers for at least one of application and removal of the stylet cap catheter connection hub.

15. A method of utilizing a catheter assembly, the method comprising:
 inserting at least a portion of a stylet coupled to a stylet cap into a catheter to position the distal end of the stylet at substantially a first location in the catheter;
 removing the stylet from the catheter;
 inserting the stylet into the catheter through a catheter connection hub having a portion of the catheter received therein and having an annular connection portion at one end thereof; and
 securing a portion of the stylet cap to the catheter connection hub comprising engaging at least one securing member of the stylet cap with only a portion of the annular connection portion of the catheter connection hub to again position the distal end of the stylet at substantially the first location in the catheter.

16. The method according to claim 15, wherein engaging at least one securing member of the stylet cap with only a portion of the annular connection portion of the catheter connection hub comprises engaging a protrusion formed at a distal end of the at least one securing member with a complementary protrusion formed on the annular connection portion of the catheter connection hub.

17. The method according to claim 15, further comprising, after engaging the at least one securing member of the stylet cap with only the portion of the annular connection portion of the catheter connection hub:
- disengaging the at least one securing member of the stylet cap from the portion of the annular connection portion of the catheter connection hub; and
- removing the stylet from within the catheter.

18. The method according to claim 17, wherein at least one of engaging the at least one securing member of the stylet cap to the portion of the annular connection portion of the catheter connection hub and disengaging the at least one securing member of the stylet cap from the portion of the annular connection portion of the catheter connection hub comprises at least partially elastically deforming a portion the at least one securing member of the stylet cap.

* * * * *

UNITED STATES PATENT AND TRADEMARK OFFICE
CERTIFICATE OF CORRECTION

| | | Page 1 of 1 |
|---|---|---|
| PATENT NO. | : 9,333,323 B2 | |
| APPLICATION NO. | : 14/354527 | |
| DATED | : May 10, 2016 | |
| INVENTOR(S) | : Sandor N. Racz et al. | |

It is certified that error appears in the above-identified patent and that said Letters Patent is hereby corrected as shown below:

On the title page:
In ITEM (54);
    LINE 3,                     change "ASSSEMBLIES, AND" to
                                     --ASSEMBLIES, AND--

In the specification:
    COLUMN 1,   LINE 3,     change "ASSSEMBLIES, AND" to
                                     --ASSEMBLIES, AND--

In the claims:
CLAIM 8,    COLUMN 12,  LINE 64,    change "connected to, the" to --connected to the--
CLAIM 14,  COLUMN 14,  LINE 45,    change "stylet cap catheter" to --stylet cap from the catheter--

Signed and Sealed this
Nineteenth Day of July, 2016

Michelle K. Lee
*Director of the United States Patent and Trademark Office*